Figure 1:
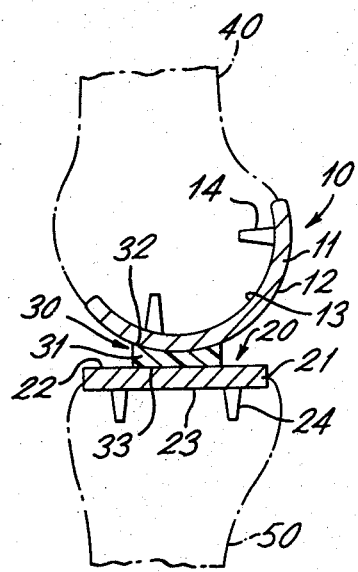

United States Patent [19]

Goodfellow et al.

[11] 4,085,466
[45] Apr. 25, 1978

[54] PROSTHETIC JOINT DEVICE

[75] Inventors: John William Goodfellow, Woodeaton; John Joseph O'Connor, Oxford, both of England; Nigel Graham Shrive, NW. Calgary, Canada

[73] Assignee: National Research Development Corporation, London, England

[21] Appl. No.: 821,905

[22] Filed: Aug. 4, 1977

Related U.S. Application Data

[63] Continuation-in-part of Ser. No. 633,034, Nov. 18, 1975, abandoned, which is a continuation-in-part of Ser. No. 632,824, Nov. 17, 1975, abandoned.

[30] Foreign Application Priority Data

Nov. 18, 1974 United Kingdom ............... 49795/74

[51] Int. Cl.² .................................................. A61F 1/24
[52] U.S. Cl. ......................................... 3/1.91; 3/1.911; 3/22; 128/92 C
[58] Field of Search ............................. 3/1, 1.9–1.913, 3/22; 128/92 C, 92 CA

[56] References Cited

U.S. PATENT DOCUMENTS

| | | | |
|---|---|---|---|
| 3,715,763 | 2/1973 | Link | 3/1.911 |
| 3,728,742 | 4/1973 | Averill et al. | 3/1.911 |
| 3,837,009 | 9/1974 | Walker | 3/1.911 |
| 3,867,728 | 2/1975 | Stubstad et al. | 3/1.91 |
| 3,868,730 | 3/1975 | Kaufer et al. | 3/1.91 |
| 3,916,451 | 11/1975 | Buechel et al. | 3/1.91 |

FOREIGN PATENT DOCUMENTS

| | | | |
|---|---|---|---|
| 1,122,634 | 5/1956 | France | 128/92 C |
| 2,122,390 | 1/1973 | Germany | 3/1.911 |

*Primary Examiner*—Ronald L. Frinks
*Attorney, Agent, or Firm*—Cushman, Darby & Cushman

[57] ABSTRACT

A prosthetic joint device is provided with first and second components respectively providing convex and relatively flat articulatory bearing surfaces, and a third component is located between the former components and has two surfaces which are complementary to and engage the convex and flat surfaces. Preferably the two pairs of engaged surfaces are suitably respectively spherically shaped and planar. The device can move under natural muscular and ligamentous control, in a varying manner closely simulating that of a natural joint which maintains uniform load distribution. Initial development centered on the provision of a knee joint endoprosthesis, but the mechanics of the device are well suited to other joints, particularly of non-congruous form, and also to joints in exoprostheses.

11 Claims, 4 Drawing Figures

PROSTHETIC JOINT DEVICE

This application is a continuation-in-part of patent application Ser. No. 633,034 filed Nov. 18, 1975, now abandoned which, in turn, is a continuation-in-part of patent application Ser. No. 632,824, filed Nov. 17, 1975, now abandoned and concerns prosthetic joint devices.

Work on the hip joint has revealed a close association between the geometry of the articulatory surfaces, the load distribution across these surfaces, and the patterns of degeneration observed in the population. A fundamental feature of the hip joint is that the surfaces exhibit a fine incongruity which enables the contact areas to grow with increasing loads, and at large loads, when all the available cartilage on the acetabulum is in contact, the distribution of cartilage thickness appears to be such that a state of uniform pressure is achieved (A. S. Greenwald and J. J. O'Conner, "The transmission of load through the human hip joint", J. Biomechanics, 1971, 4, 507 – 528).

Similar geometrical design has been discussed in the elbow joint and appears to be an important feature of joint design in man and other animals (J. W. Goodfellow and P. G. Bullough, "The pattern of ageing in the articular cartilage of the elbow joint", and J. J. O'Conner, "The relationship between degenerative changes and load bearing in the human hip", J. Bone and Joint Surgery, 1973, 55B, 746).

However, the knee joint appears to be an exception to this more general rule, unless it can be shown that the menisci play a significant role in the transmission of load. Work leading to conception of the present invention has demonstrated that this is, in fact, the case and that in the loaded situation the menisci do transmit a considerable proportion of the load. Any resultant tendency for the femoral condyles to push the menisci radially outwardly is resisted by circumferential tension in the menisci.

Now it is reasonable to presume that, among other things, an ideal prosthesis would reproduce the physiological range, modes and axes of movement, and also the normal pattern of load bearing of the natural joint. The mode and axis of movement in the human knee is complex and changing, and in any one position depends both upon the geometry of the articulatory surfaces and the direction and magnitude of the tensile forces developed in the associated muscles and ligaments. Accordingly, the ideal prosthesis can be regarded as reproducing as accurately as possible the geometry of the relevant surfaces, while interfering as little as possible with the continued function of the muscles and ligaments and, at the same time, maintaining a reasonably uniform distribution of load.

A review of previously proposed knee joint prostheses employed in clinical practice indicates that this ideal is not attained. Earlier proposals involve hinge devices which constrain the motion to simple pivotal rotation about a single axis. Such hinge devices have, in any case, led to an unacceptable failure rate. More recent proposals seek to remedy the failures of hinge devices, and involve two components which are respectively connected with the femur and tibia and held in engagement by the muscles and ligaments to produce a more life-like situation. However, these more recently proposals face a contradictory requirement in that matching of the engaged surfaces of the components to afford uniform load distribution allows little freedom for variation in the mode and axis of movement, while incongruence between the surfaces to suit the requirements of movement necessarily reduces and/or varies the surface contact area with consequently disadvantageous load distribution.

An object of the present invention is to reduce the difficulties of this situation by providing a device which allows a closer approach to attainment of the ideal.

To this end, the invention provides a prosthetic joint device, comprising a first component having a generally convexly curved articulatory bearing surface, a second component having a relatively flattened articulatory bearing surface compared to that of said first component, and a third component having two articulatory bearing surfaces in back-to-back disposition and of individual forms respectively substantially complementary to said first and second component articulatory surfaces.

In use of the invention in a knee joint endoprosthesis, the first and second components are to be secured respectively with the femur and tibia with the articulatory surfaces of these components in facing disposition, and the third component will be located therebetween to serve as a meniscal component with its articulatory bearing surfaces in respective engagement with those of the former components.

The consequences of this arrangement are that:

(1) The femoral and meniscal components, and the meniscal and tibial components, are capable of independent relative movement by virtue of the complementary nature of the two pairs of engaged surfaces. More particularly, the femoral and meniscal components are capable of mutual rotation about three orthogonal axes, and the meniscal and tibial components are capable of mutual sliding in two of the relevant axial directions and mutual rotation about the third of such axial directions. The resultant capability for relative movement between the femoral and tibial components is accordingly extensive and can embrace rolling, gliding, twisting, and combinations thereof, such as are found in the knee joint.

(2) The generally convex and relatively flattened shapings of the femoral and tibial component bearing surfaces can reproduce the natural shapings of the natural femoral and tibial condyles sufficiently closely that the complete interactions between the surface shapes and the forces in the surrounding muscles and ligaments, which control the stability of the joint, will be life-like.

(3) The complementary nature of the engaged surfaces of the components is such that a relatively uniform distribution of surface pressure is achieved in all positions of these components.

(4) The meniscal component is entrapped between the femoral and tibial components by virtue of the complementary convex-concave shaping of the engaged femoral-meniscal component surfaces and the different, relatively flattened, complementary shaping of the engaged meniscal-tibial component surfaces.

Development of the invention since its initial conception has shown that, while a variety of prospectively advantageous forms are possible within the more general scope of the invention, the above consequences can result from a relatively simple form of the invention in which the engaged femoral and meniscal bearing surfaces are part-spherically shaped, and the engaged meniscal and tibial component bearing surfaces are planar.

Moreover, continued development of the invention has shown that the mechanics of the device initially conceived for the knee joint are advantageous in application to other joints. This more general application of the invention is particularly relevant to joints of an incongruous form involving two bones with mutually co-operating articular surfaces which are respectively convexly shaped and relatively flattened or somewhat concavely shaped. In addition to the knee, such joints are found in the shoulder, the wrist, the ankle, the fingers, and the toes.

The relevance of this more general application of the invention is based on a particular view of the form and function of the basic elements of the joints in question, these elements being the articular surfaces and adjacent bone, the ligaments, and the tendons through which the muscles act on the bones. This view holds that the articular surfaces allow substantially all movements except mutual interpenetration, with the adjacent bone serving predominantly to transmit compressive forces, and that the other elements control and limit the surface movements while themselves serving to resist and transmit tensile forces. Thus, there is an interdependence between the elements of a joint, and this interdependence is vital to the overall performance of a joint having incongruent surfaces which can provide little inherent stability.

There is support for the above view in the following facts:

(a) The incongruous joints in question each involve at least one elongate bone and such bones have their articular surfaces on bulbous regions at the ends of shafts.
(b) The bulbous regions are formed predominantly of trabecular bone with a relatively thin casing of cortical bone, while the shafts comprise thick tubular structures of cortical bone.
(c) The trabeculae of the bone adjacent to the articular surfaces is aligned generally perpendicularly thereto and this alignment continues to the shaft. This structure is singularly well adapted to resist and transmit compressive stress and contrasts with that of the shaft which has a general ability to transmit compressive, tensile and shear stresses.
(d) The ligament connections to an elongate bone in a joint are generally found at the region where the shaft joins the bulbous region.

Application of the invention in this context is advantageous in that substantially only compressive force is transmitted by the device, and the first and second components can be substituted for the convex and relatively flattened articular surfaces for optimum compatibility with the adjacent bone structure. At the same time, the third component can be selected from a range having differing thicknesses to ensure that there is no undue laxity in the ligaments and tendons such as would otherwise render the prosthesis unstable.

Given the above-proposed more general application of the invention and its advantage in affording complex motion capabilities, yet further development also indicates the possibility of application as an exoprosthetic joint in an artificial limb. This has particular relevance to the knee joint in an artificial leg where rotatory movement about the longitudinal axis is not catered for in prior art designs. Naturally, since there are no ligaments and tendons in an artificial limb, the present device will require the addition of tensile elements interconnecting the first and second components for stability. Similar considerations apply to an exoprosthesis of so-called "orthotic" form used to assist, rather than replace, a natural joint function.

Figure 2:
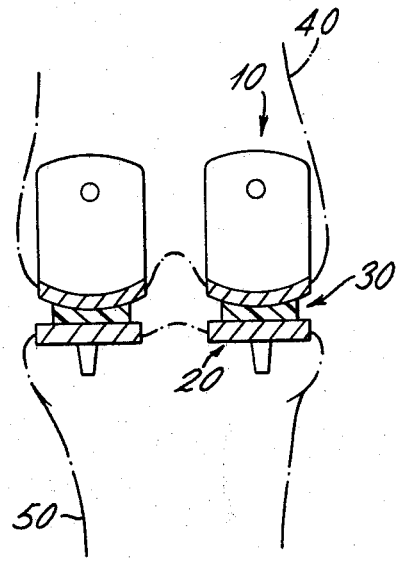
Figure 3:
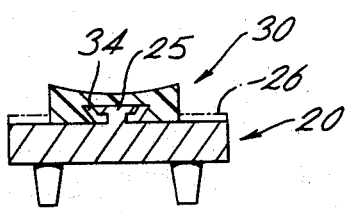
Figure 4:
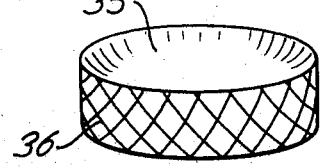

In order that the invention may be fully and clearly understood, the same will now be described by way of example with reference to the accompanying drawings, in which:

FIGS. 1 and 2 are respective mutually-perpendicular, schematic cross-sectional views of one embodiment of the above simple form of the invention as applied to an endoprosthetic knee joint device, FIG. 3 schematically illustrates a modification of such embodiment, and FIG. 4 illustrates another modification of such embodiment.

The embodiment of FIGS. 1 and 2 is a bicondylar device comprising two sets of components for use in respective substitution for the lateral and medial condyles and menisci of the natural knee joint. The two sets of components can be identical and so, for convenience, the structural form of only one set will be described.

In the relevant set, the femoral, tibial and meniscal components are respectively denoted by reference numerals 10, 20 and 30. Also shown in FIGS. 1 and 2 in broken outline are the associated distal end portions of the femur and the proximal end portion of the tibia at 40 and 50, respectively.

The femoral component comprises a bearing body 11 in the general form of a longitudinally curved strip of which the convex face defines a part-spherically shaped surface 12 to serve as an articulatory bearing surface. The concave face of the body 11 serves as a fixation surface 13 adapted for securement to the femur in accordance with existing techniques so that the surface 12 serves as a femoral condylar surface replacement. In the present instance this securement is to be effected with the use of acrylic bone cement and for this purpose the surface is formed with one or more intracancellous stems 14 integrally projecting therefrom, and the surface 13 is also grooved.

The tibial component 20 comprises a bearing body 21 in the form of a D-shaped platform of generally uniform thickness. One face of the body 21 defines a planar surface 22 to serve as an articulatory bearing surface. The other face of the body 21 serves as a fixation surface 23 adapted for securement to the tibia, in accordance with similar techniques to those for the femoral component, so that the surface 22 serves as a tibial condylar surface replacement. For this purpose the surface 23 is formed with one or more intracancellous stems 24 integrally projecting therefrom.

The meniscal component 30 comprises a bearing body 31 in the form of a circular disc. One face of this body is concavely part-spherically shaped to the same radius as the surface 12 of the femoral component to serve as an articulatory bearing surface 32 engaged with the surface 12. The other face of the body 31 is planar to serve as an articulatory bearing surface engaged with the surface 22 of the tibial component.

In use of these components the femoral and tibial components are secured to suitably prepared sites in the femur and tibia, and the meniscal component is then engaged therebetween. The overall surgical procedure need involve no special requirements since this procedure can be similar to those already developed for existing bicondylar knee joint devices such as the so-called 'Polycentric' prosthesis devised by Gunston.

A primary advantage of the illustrated device results from the first three consequences noted above, namely, that the movements of the natural joint can be closely simulated without significant distortion of the natural controlling and stabilizing mechanisms while, at the same time, uniform distribution of surface pressure is maintained through the device. In so far as the shaping of the component bearing surfaces do not precisely reproduce the natural condylar shapings, there can be some differences in the respective overall positional relationships between these shapings for a given operating condition of the muscles and ligaments during the flexion-extension cycle. However, these differences will be very minor and this has been confirmed by a cadaveric trial in which the known characteristics of the natural joint movement were clearly exhibited. Thus: the femoral component rotated with little translational movement relative to the tibial component during initial extension the femoral component continued to rotate with increasing forward translation of the meniscal component during further extension so that the axis of femoral-tibial rotation moved forwardly on the tibia; the latter translation was accompanied by a transverse rotation near full extension so that the tibia twisted relative to the femur about the longitudinal axis of the leg as in the so-called 'screw home' action; and a reverse sequence of events occurred.

It is to be noted that, while this sequence of events entails relative rolling, sliding, and twisting between the femur and tibia, the components of the device are only subjected to sliding movements under uniform pressure distribution. Accordingly, as a further advantage, there will be no undue dynamic stresses leading to accelerated wear in the components.

Other advantages stem from the meniscal component. This component is readily replaceable by way of simple surgery to take account of wear. Further advantage can be taken of this fact by making the meniscal component of plastics material and the other components of metal so that the interfaced materials can provide known low friction properties, the secured components will be inherently stable, and the more likely long-term wear will occur in the more readily replaceable component.

A further advantage stemming from the meniscal component is that this component can be made available in a range of different thicknesses and the surgeon can select from this range to tension the capsule appropriately, particularly to avoid undue laxity, and also to correct any varus or valgus deformity.

Yet another advantage of the illustrated device is that the surgeon is relieved and the requirement to locate the femoral and tibial components in a closely prescribed positional relationship when securing the same. This requirement normally arises with existing devices, but the meniscal component of the present device serves as a self-adjusting intermediary to accommodate different positional relatinships between the other two components.

While the invention has been described with more particular reference to the illustrated embodiment, it is not intended that the invention be limited thereby. The provision of the invention in a bicondylar device form is presently preferred since this form offers special advantages in the ability to retain the cruciate ligaments and the absence of an inherent requirement for patella detachment for the purposes of component securement. However, even in this form, the device can be varied from the illustrated embodiment.

One such variation is illustrated by FIG. 3 in which modified tibial and meniscal components are shown. The modification involves the provision of a generally mushroom-shaped projection 25 from the central zone of the tibial component bearing surface 22. This projection is engaged in an undercut recess 34 in the meniscal component. The mouth of the recess has a diameter significantly larger than that of the projection stem, but is slightly smaller than that of the projection head, so that engagement of the projection and recess involves a snap action whereafter relative sliding movement can occur in all directions of the surfaces 22 and 33 up to the limits imposed by abutment of the projection with the recess side wall. Preferably the projection and recess are of equal depth with planar surfaces at their respective free end and base, which surfaces are parallel to the surfaces 22 and 33 so that the former surfaces are slidably engaged when the latter surfaces are similarly engaged.

Although it is considered that the meniscal component of an embodiment such as that of FIGS. 1 and 2 can be adequately captively retained between the other two components, the modification of FIG. 3 can provide enhanced stability without compromising the desired motion capabilities. The preferred sliding engagement between the projection and recess maintains the area of contact between the tibial and meniscal components relative to FIGS. 1 and 2, and in fact slightly increases this area.

A similar stabilizing arrangement can be affected between the meniscal and femoral components by use of a projection from surface 32 and a slotted recess in surface 12.

Stability of the meniscal component can also be enhanced by elongating this component to an oval form in plan view so that the curved area of contact with the femoral component, which is a basic cause of meniscal component entrapment, is increased. In use, this elongation is preferably maintained in a generally anteroposterior attitude and, for this purpose, it may be appropriate to provide the tibial component with a raised side wall, as indicated at 26 in FIG. 3, to limit the extent to which the meniscal component can spin.

Enhanced stability in a lateral sense may also be provided in a bicondylar device according to the invention by mutually laterally inclining the interface between the tibial and meniscal component surfaces 22 and 33. While this can be effected by the provision of appropriately inclined sites on the tibia for tibial components of uniform thickness, generally wedge-shaped tibial components can be provided for use in more conventionally disposed sites.

Also, it will be appreciated that the proposed form of bicondylar device is not limited to use of particular securement techniques or specific materials.

The invention is also applicable to other than bicondylar devices. In a simple form the invention can be applied to a device having a singular set of components for the whole knee (as in the so-called ICLH device); a bicondylar form can be modified by integrating some or all of the corresponding components while providing slotted component structures for retention of the cruciate ligaments (as in the so-called 'Geomedic' device); the bearing surface of the femoral component can be of varying curvature and differ at least in part from that with which it articulates (as in the ICLH device); and the engaged surfaces of the tibial and meniscal components need not necessarily be planar, but these surfaces will be relatively flat compared to the other engaged surfaces. These variations will not necessarily afford all of the advantages discussed above, but it is clearly possible to obtain advantage relative to the nearest equivalent device among those previously proposed.

Also, modification can be made by the use of resilient plastics material for the meniscal component so that this component can comply with changing geometry, particularly in an associated femoral surface, during articulation. Preferably, any such resilience should reside predominantly in the longitudinal axial direction relative to the leg, that is, generally perpendicularly relative to the meniscal component bearing surfaces, while the component is relatively stiff circumferentially to restrain radially outward components of load as in the natural menisci. Such differential resilience may be achieved with a circumferentially fibre-reinforced plastics construction, such as is shown in FIG. 4, wherein silastic rubber component 35 is disposed within an annular sock 36 of nylon or other synthetic fibre. Moreover, such a meniscal component may find application alone for engagement between the natural femoral and tibial condyles in treatment of conditions such as those which result from sporting activity, and are currently treated by so-called cartilage removal.

We claim:

1. A prosthetic joint device comprising:
 a first component having a generally convex articulatory bearing surface;
 a second component having a relatively flattened articulatory bearing surface compared to that of said first component;
 and a third component having two articulator bearing surfaces in back-to-back disposition and of individual forms substantially complementary to said first and second component articulatory surfaces, said third component being located between said first and second components with the two pairs of said complementary surfaces freely slidably and individually non-captively engaged.

2. A device according to claim 1 wherein said first component surface and said third component surface complementary thereto are each part-spherically shaped to equal radii of curvature.

3. A device according to claim 1 wherein said second component surface and said third component surface complementary thereto are each planar.

4. A device according to claim 1 wherein each of said first and second components is of integral metal construction, and said third component is of integral plastics material construction.

5. A device according to claim 1 wherein said third component is in the form of a disc of resilient material which disc is circumferentially reinforced to restrain radially outward movement of said material otherwise caused by varying patterns of axially-directed load thereon.

6. A prosthetic joint device comprising:
 a first component having a generally convex articulatory bearing surface;
 a second component having a relatively flattened articulatory bearing surface compared to that of said first component.
 a third component having two articulatory bearing surfaces in back-to-back disposition and of individual forms respectively substantially complementary to said first and second component articulatory surfaces, said third component being located between said first and second components with the two pairs of said complementary surfaces engaged for sliding articulatory movement therebetween;
 and a linkage between said third component and one of said first and second components, such linkage including a projection from the respective bearing surface of one of the linked components, and a recess in the respective bearing surface of the other of the linked components, said projection extending into said recess and being laterally movable therein.

7. A device according to claim 6 wherein said projection extends from said second component, and said recess is formed in said third component.

8. A device according to claim 7 wherein said projection is generally mushroom shape, and said recess is undercut to receive said projection by a snap fit.

9. An endoprosthetic bone joint device for a joint of non-congruous form having first and second bones with respective articular surfaces of individually greater and lesser curvature, said device comprising:
 a first component having a convex part-spherical articulatory bearing surface, and adapted for securement to said first bone to substitute said surface of greater curvature;
 a second component having a first planar articulatory bearing surface, and adapted for securement to said second bone to substitute said surface of lesser curvature;
 and a third component having two articulatory bearing surfaces in back-to-back disposition, one of said two surfaces being of concave part-spherical shape with equal curvature to said convex surface, and the other of said two surfaces being a second planar surface;
 said components each being of one-piece construction;
 and said third component being located between said first and second components with said convex and concave surfaces, and said first and second planar surfaces, respectively in complementary free-sliding, individually non-captive engagement.

10. An endoprosthetic knee joint device, comprising:
 a femoral condylar component adapted for securement to the femur and defining two like convex part-spherical articulatory bearing surfaces in spaced side-by-side disposition;
 a tibial condylar component adapted for securement to the tibia and defining two like first planar articulatory bearing surfaces in spaced side-by-side disposition facing said convex surfaces to form two pairs of facing surfaces;
 and two like meniscal components each defining two articulatory bearing surfaces in back-to-back disposition, one of such two surfaces being of concave part-spherical shape with equal curvature to said convex surfaces, and the other of such two surfaces being a second planar surface;
 said meniscal components being located and held between said femoral and tibial components in side-by-side disposition, with said concave surface and said second planar surface of each of said meniscal components in respective sliding engagement with said convex surface and said first planar surface of a different one of said two pairs of facing surfaces.

11. A device according to claim 10, wherein said femoral component comprises two like separate sub-components respectively defining said convex surfaces, and said tibial component comprises two like separate sub-components respectively defining said first planar surfaces.

* * * * *